(12) United States Patent
Kelly et al.

(10) Patent No.: US 6,987,078 B2
(45) Date of Patent: Jan. 17, 2006

(54) ALKYLATION AND CATALYST REGENERATIVE PROCESS

(75) Inventors: Kevin P. Kelly, Friendswood, TX (US); James R. Butler, Houston, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

(21) Appl. No.: 10/678,577

(22) Filed: Oct. 3, 2003

(65) Prior Publication Data

US 2005/0075237 A1   Apr. 7, 2005

(51) Int. Cl.
- *B01J 20/34* (2006.01)
- *B01J 38/12* (2006.01)
- *B01J 38/14* (2006.01)

(52) U.S. Cl. .......................................... 502/38; 502/52
(58) Field of Classification Search .................. 502/38, 502/52
See application file for complete search history.

(56) References Cited

U.S. PATENT DOCUMENTS

| | | | |
|---|---|---|---|
| 3,308,069 A | 3/1967 | Wadlinger et al. | |
| 4,169,111 A | 9/1979 | Wight | |
| 4,185,040 A | 1/1980 | Ward et al. | |
| 4,642,226 A | 2/1987 | Calvert et al. | |
| 4,798,816 A | 1/1989 | Ratcliffe et al. | |
| 4,849,385 A * | 7/1989 | Huang et al. | 502/35 |
| 4,891,458 A | 1/1990 | Innes et al. | |
| 4,973,780 A * | 11/1990 | Johnson et al. | 585/467 |
| 5,030,786 A | 7/1991 | Shamshoum et al. | |
| 5,073,653 A | 12/1991 | Butler | |
| 5,087,783 A * | 2/1992 | Johnson et al. | 585/475 |
| 5,256,392 A | 10/1993 | Shamshoum | |
| 5,326,923 A * | 7/1994 | Cooper et al. | 585/725 |
| 5,365,010 A * | 11/1994 | Rao et al. | 585/726 |
| 5,405,814 A * | 4/1995 | Beech et al. | 502/53 |
| 5,648,585 A * | 7/1997 | Murray et al. | 585/671 |
| 5,900,518 A | 5/1999 | Merrill et al. | |
| 5,907,073 A | 5/1999 | Ghosh | |

(Continued)

FOREIGN PATENT DOCUMENTS

| | | |
|---|---|---|
| EP | 0159846 A2 | 10/1985 |
| EP | 0186447 A2 | 7/1986 |
| EP | 0507761 A1 | 10/1992 |

OTHER PUBLICATIONS

Liu et al., "On the Thermal Stability of Zeolite Beta," Journal of Catalysis, vol. 132, pp. 432-439, 1991.

(Continued)

*Primary Examiner*—Thuan D. Dang
*Assistant Examiner*—Jonas N. Strickland
(74) *Attorney, Agent, or Firm*—William D. Jackson

(57) ABSTRACT

A process for the regeneration of a deactivated zeolite beta catalyst such as rare earth promoted zeolite beta catalyst deactivated in the course of an aromatic alkylation reaction. A zeolite beta conversion catalyst deactivated with the deposition of coke is heated to a temperature in excess of 300° C. in an oxygen-free environment. An oxidative regeneration gas is supplied to the catalyst bed with oxidation of a portion of a relatively porous coke component to produce an exotherm moving through the catalyst bed. At least one of the temperature and oxygen content of the gas is progressively increased to oxidize a porous component of the coke. Regeneration gas is supplied having at least one of an increased oxygen content or increased temperature to oxidize a less porous refractory component of the coke. The regeneration process is completed by passing an inert gas through the catalyst bed at a reduced temperature.

15 Claims, 7 Drawing Sheets

U.S. PATENT DOCUMENTS 5,955,642 A    9/1999   Merrill et al.
6,137,020 A    10/2000  Butler et al.
6,222,084 B1 * 4/2001   Ghosh et al. ............... 585/323
6,245,703 B1 * 6/2001   Kuechler et al. ............. 502/22
6,376,729 B1   4/2002   Merrill et al.
6,835,363 B1 * 12/2004  Strohmaier ................ 423/305

OTHER PUBLICATIONS

Higgins et al., "The Framework Topology of Zeolite Beta," Zeolites, vol. 8 (Nov.), pp. 446-452, 1988.

Meier et al., "Atlas of Zeolite Structure Types," p. 58, 3rd. Ed., 1992, Butterworth-Heinemann.

* cited by examiner

◇ Ce/beta
□ La/beta
— Linear (Ce/beta)

- ◆ fresh catalyst
- ■ after 1 regen
- △ after 2 regen's
- × after 3 regen's
- □ after 4 regen's
- ○ after 5 regen's-high temp
- ◇ after 6 regen's-high temp, upflow
- ▭ after quick burn
- + after 7 regen's-high temp
- ● After 8 regens-upflow
- —— Linear (fresh catalyst)
- —— Linear (after 5 regen's-high temp)

◇ heavies Ce/beta
☐ heavies La/beta
△ heavies silicalite

◇ TEB Ce/beta
☐ TEB La/beta

ALKYLATION AND CATALYST REGENERATIVE PROCESS

FIELD OF THE INVENTION

This invention relates to the regeneration of a deactivated zeolite beta catalyst and more particularly to catalyst regeneration in conjunction with the production of ethylbenzene including the ethylation of benzene over a cerium- or lanthanum-promoted beta alkylation catalyst under the conditions in which the benzene can be in the gas phase, the liquid phase, or the supercritical phase.

BACKGROUND OF THE INVENTION

The alkylation of benzene with ethylene over a molecular sieve catalyst is a well-known procedure for the production of ethylbenzene. Typically, the alkylation reaction is carried out in a multistage reactor involving a feedstream of benzene and ethylene to the front of the reactor with the interstage injection of ethylene and benzene to produce an output from the reactor that involves a mixture of monoalkyl and polyalkylbenzene. The principal monoalkylbenzene is, of course, the desired ethylbenzene product. Polyalkylbenzenes include diethyl benzene, triethylbenzene, and xylenes.

With the passage of time, the catalyst becomes deactivated. The alkylation reaction is an exothermic reaction which is accompanied by the deposition of coke on the catalyst bed. The degree of deactivation can be determined by sensing the exotherm as it moves progressively through the catalyst bed from the inlet side to the outlet side of the reactor.

In many cases, it is desirable to operate the alkylation reactor in conjunction with the operation of a transalkylation reactor in order to produce additional ethylbenzene through the transalkylation reaction of polyethylbenzene with benzene. The alkylation reactor can be connected to the transalkylation reactor in a flow scheme involving one or more intermediate separation stages for the recovery of ethylene, ethylbenzene, and polyethylbenzene.

Transalkylation may also occur in the initial alkylation reactor. In this respect, the injection of ethylene and benzene between stages in the alkylation reactor not only results in additional ethylbenzene production but also promotes transalkylation within the alkylation reactor in which benzene and diethylbenzene react through a disproportionation reaction to produce ethylbenzene.

Various phase conditions may be employed in the alkylation and transalkylation reactors. Typically, the transalkylation reactor will be operated under liquid phase conditions, i.e., conditions in which the benzene and polyethylbenzene are in the liquid phase, and the alkylation reactor is operated under gas phase conditions, i.e., pressure and temperature conditions in which the benzene is in the gas phase. However, liquid phase conditions can be used where it is desired to minimize the yield of undesirable by-products from the alkylation reactor.

SUMMARY OF THE INVENTION

In accordance with the present invention, there is provided a process for the regeneration of a deactivated zeolite beta catalyst, and particularly for the regeneration of a rare earth promoted zeolite beta catalyst deactivated in the course of the alkylation of an aromatic substrate with a $C_2$–$C_4$ alkylating agent. In carrying out the invention, there is provided a zeolite beta conversion catalyst which has been deactivated in a hydrocarbon conversion reaction with the deposition of coke on the catalyst. The coke has a porosity characteristic ranging from a relatively porous constituent to a relatively less porous refractory coke constituent. The catalyst is heated to a temperature in excess of 300° C. in an inert environment which is substantially free of oxygen. Subsequently, an oxidative regeneration gas comprising a mixture of an oxygen containing gas, preferably air, and an inert gas, preferably nitrogen, is supplied to the catalyst bed. The regeneration gas oxidizes at least a portion of the relatively porous coke component at a temperature greater than the initial heating temperature, and produces an exotherm which moves through the catalyst bed. The supply of regeneration gas is continued to result in decoking of the zeolite catalyst while progressively increasing at least one of the temperature and the oxygen content of the regeneration gas to oxidize a less porous component of the coke with the production of an exotherm which moves through the catalyst bed. As the regeneration process is continued, regeneration gas is supplied having at least one of an increased oxygen content or an increased temperature greater than the temperature or oxygen content previously supplied to oxidize a less porous refractory component of the coke. The regeneration process is completed by diminishing the oxygen content of the regeneration gas and passing an inert gas through the catalyst bed at a reduced temperature.

In one embodiment of the invention, the regeneration gas is introduced into the catalyst bed at an elevated temperature of at least 500° C., preferably about 525–575° C., and the oxygen content of the regeneration gas is progressively increased from a very low level to a substantially greater level. In the preferred embodiment of the invention in which the regeneration gas is a mixture of air and nitrogen, the regeneration procedure is initiated by the initial introduction of nitrogen at a temperature of at least 500° C. Air is added in a small amount to provide an initial air content of no more than 5 vol. %. During the initial phase of the regeneration procedure, a relatively porous coke component is oxidized. During the latter stages of the regeneration procedure with the air content increased within the range of 40–60 wt. %, preferably about 50 wt. % nitrogen, a less porous, more refractory component of the coke is oxidized.

In a preferred application of the present invention, the regeneration procedure is carried out in conjunction with the alkylation of an aromatic substrate with a $C_2$–$C_4$ alkylating agent. A specific application of the present invention involves the production of ethylbenzene. The production of ethylbenzene may be carried out in the gas phase, liquid phase or supercritical phase. Preferably the production of ethylbenzene will be carried out in a liquid phase or supercritical phase alkylation reaction. In this aspect of the invention, there is provided an alkylation reaction zone incorporating a catalyst bed of a zeolite beta alkylation catalyst. Preferably, the zeolite beta is promoted with lanthanum or cerium. More preferably, the zeolite beta catalyst is a cerium promoted catalyst having a silica/alumina mole ratio within the range of 20–500, and more preferably within the range of 50–200. The cerium promoted zeolite beta catalyst has a cerium/aluminum atomic ratio within the range of 0.5–1.5.

In carrying out this embodiment of the invention, an aromatic feedstock containing benzene is supplied into the catalyst bed at an inlet side of the reaction zone. Ethylene is also supplied to the catalyst bed at the inlet side of the reaction zone. The alkylation reaction zone is operated at temperature and pressure conditions in which benzene is in the liquid phase or super critical phase, preferably the latter, to cause ethylation of the benzene by an exothermic reaction with the production of an exotherm which passes through the catalyst bed in a direction from the inlet side to the outlet side of the reaction zone. The supply of benzene and ethylene is continued until the exotherm traverses a substantial portion of the catalyst bed. Thereafter, the supply of ethylene and benzene is terminated, and an inert gas is supplied to the reaction zone to provide temperature conditions in the reactor which are initially lower than the temperature conditions at the conclusion of the alkylation procedure. Preferably, in terminating the supply of ethylene and benzene to the alkylation reaction zone, the ethylene supply is terminated prior to the benzene supply. Subsequent to initiating the inert gas introduction, the temperature in the reaction zone is increased and a supply of an oxidative regeneration gas comprising a mixture of oxygen and inert gas is introduced into the catalyst bed to produce an exotherm which moves through the catalyst bed. Preferably, the oxygen containing gas is air and the inert gas is nitrogen, as discussed previously. In continued operation, the regeneration gas is supplied to the catalyst bed in a mixture having an increased ratio of oxygen to the inert gas to oxidize the coke at an increased temperature.

In yet a further embodiment of the present invention, the regeneration procedure is carried out, employing the alternate introduction into the catalyst bed of an inert gas, specifically nitrogen, and an oxidative regeneration gas comprising a mixture of oxygen and nitrogen. This embodiment of the invention may be carried out in conjunction with the production of ethylbenzene over a cerium promoted zeolite beta alkylation catalyst in which the alkylation reaction zone is operated in the gas phase, liquid phase or supercritical phase. In this embodiment of the invention, with deactivation of the catalyst, the supply of benzene and ethylene to the reaction zone containing the catalyst bed is terminated. After benzene injection at the conclusion of the alkylation procedure is terminated, nitrogen is introduced into the reaction zone and nitrogen injection is continued until the benzene content within the reaction zone is substantially reduced. Thereafter, an oxidative regeneration gas combining a mixture of oxygen and nitrogen is introduced into the catalyst bed at an elevated temperature to oxidize coke on the catalyst bed and produce an exotherm which moves through the catalyst bed concurrently with the flow of oxygen and nitrogen through the catalyst bed. After the exotherm passes through a substantial portion of the catalyst bed, nitrogen is introduced into the catalyst bed at a temperature greater than the initial regeneration step to provide an incremental increase in the average temperature of the catalyst bed. The regeneration gas comprises a mixture of oxygen and nitrogen is then introduced at a temperature greater than the previous temperature to oxidize coke in the catalyst bed and produce an exotherm having a temperature greater than the temperature of the previous exotherm. After this exotherm passes through a substantial portion of the catalyst bed, nitrogen is again introduced into the catalyst bed at an elevated temperature greater than the temperature of the previous nitrogen injection step. Thereafter, a regeneration gas comprising a mixture of air and nitrogen is introduced into the catalyst bed to oxidize coke therein and produce an exotherm having a temperature greater than the previous exotherm. At the conclusion of the regeneration procedure, the operation of the reaction zone for the production of ethyl benzene is reinstituted by introducing benzene and ethylene to the inlet side of the reaction zone. Preferably, at the conclusion of the regeneration procedure and prior to reinstituting the alkylation procedure, nitrogen is introduced into the catalyst bed at a temperature which is less than the last nitrogen injection step of the regeneration procedure. In a preferred embodiment of the invention, the inert gas and the oxidative regeneration gas are introduced into the reaction zone at the outlet so that flow is from the outlet of the reaction zone to the inlet of the reaction zone in a direction which is countercurrent to the flow of benzene and ethylene during the alkylation reaction.

DETAILED DESCRIPTION OF THE INVENTION

Figure 1:
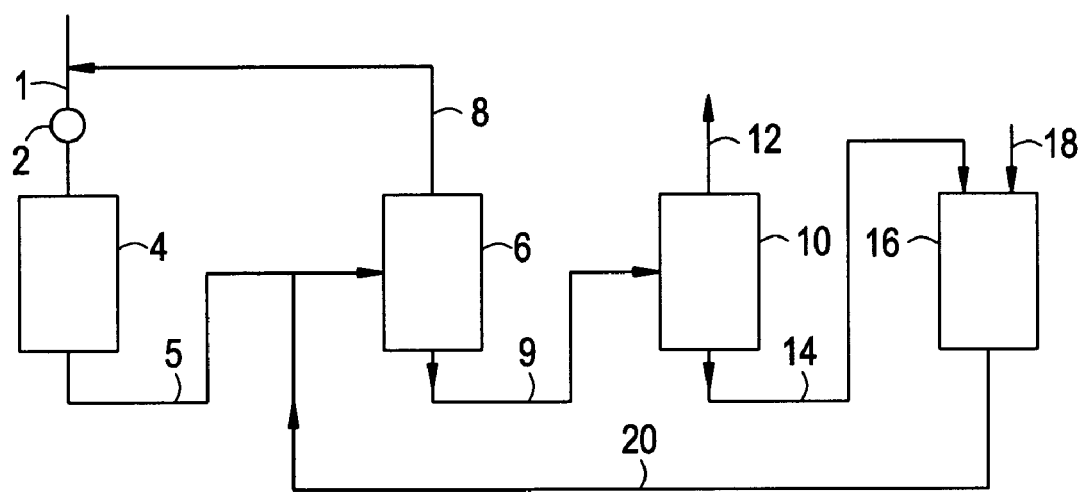
FIG. 1 is an idealized schematic block diagram of an alkylation/transalkylation process embodying the present invention.

The present invention involves the regeneration of a deactivated catalyst resulting from the use of the catalyst in a hydrocarbon conversion reaction. The invention is particularly applicable to rare earth modified zeolite betas, particularly lanthanum modified beta and cerium modified zeolite beta, employed in the alkylation of benzene. The alkylation reaction may be carried out with benzene in the gas phase, the liquid phase, or the supercritical phase. Preferably the invention will be carried out under conditions to effect alkylation of the benzene, or other aromatic substrate, in the liquid phase or supercritical phase. The regeneration procedure involved in the present invention is especially useful in the regeneration of a cerium of modified zeolite beta. Regardless of the use of a rare earth to modify the zeolite beta, the zeolite beta will preferably have a silica alumina ratio within the range of 20–500 and more preferably within the range of 50–200.

A preferred embodiment of the invention involves regeneration of a catalyst used in the critical phase alkylation of benzene over a cerium-promoted zeolite beta alkylation catalyst. Critical phase alkylation can be carried out under conditions to control and desirably minimize the yield of by-products in the alkylation reaction zone. The feedstock supplied to the alkylation reaction zone comprises benzene and ethylene. Typically, the benzene and ethylene streams will be combined to provide a benzene-ethylene mixture flowing through the reaction zone. The benzene stream, which is mixed with the ethylene either before or after introduction into the reaction zone, should be a relatively pure stream containing only very small amounts of contaminants. The benzene stream should contain at least 90 wt. % benzene. Preferably, the benzene stream will be at least 98 wt. % benzene with only trace amounts of such materials as toluene, ethylbenzene, and $C_7$ aliphatic compounds that cannot readily be separated from benzene. The alkylation reaction zone preferably is operated under supercritical conditions, that is, pressure and temperature conditions which are above the critical pressure and critical temperature of benzene. Specifically, the temperature in the alkylation zone is at or above 280° C., and the pressure is at or above 550 psia. Preferably, the temperature in the alkylation reactor will be maintained at an average value within the range of 290–350° C. after initiating the reaction and a pressure within the range of 550–850 psia. If desired, higher alkylation temperatures can be employed since the cerium-promoted zeolite beta retains its structural integrity at temperatures of about 530–540° C. Zeolite beta which has not been promoted with cerium tends to lose its structural integrity as the temperature reaches 500° C. The critical phase alkylation reaction is exothermic with a positive temperature gradient from the inlet to the outlet of the reactor, providing a temperature increment increase of about 40° C.±10°.

The operation of the alkylation reaction zone in the supercritical region enables the alkylation zone to be operated under conditions in which the benzene-ethylene mole ratio can be maintained at relatively low levels, usually somewhat lower than the benzene-ethylene mole ratio encountered when the alkylation reaction zone is operated under liquid phase conditions. In most cases, the benzene-ethylene mole ratio will be within the range of 1–15. Preferably, the benzene mole ratio will be maintained during at least part of a cycle of operation at a level within the lower end of this range, specifically, at a benzene-ethylene mole ratio of less than 10. A benzene-ethylene mole ratio within the range of 3–8 may be employed. Thus, operation in the supercritical phase offers the advantages of gas phase alkylation in which the benzene-ethylene ratio can be kept low but without the problems associated with by-product formation, specifically xylene formation, often encountered in gas-phase alkylation. At the same time, operation in the supercritical phase offers the advantages accruing to liquid phase alkylation in which the by-product yield is controlled to low levels. The pressures required for operation in the supercritical phase are not substantially greater than those required in liquid phase alkylation, and the benzene in the supercritical phase functions as a solvent to keep the zeolite beta catalyst clean and to retard coking leading to deactivation of the catalyst.

As indicated by the experimental work described later, the cerium-promoted beta enables supercritical phase alkylation to be carried out with by-products that are substantially less than the corresponding by-products produced with supercritical phase alkylation employing lanthanum-promoted zeolite beta of similar or greater content. Thus, the alkylation reaction zone can be operated at supercritical phase temperature and pressure conditions to provide a composite by-product yield of propylbenzene and butylbenzene which is less than the corresponding composite by-product yield of propylbenzene and butylbenzene for a corresponding zeolite beta catalyst promoted with lanthanum at a lanthanum/aluminum atomic ratio at least as great as the cerium/aluminum atomic ratio of the cerium-promoted zeolite beta. In employing cerium-promoted zeolite beta, the alkylation reaction zone preferably is operated at temperature and pressure conditions to provide a composite product yield of propylbenzene and butylbenzene which is no more than one-half of the corresponding composite by-product yield of propylbenzene and butylbenzene produced with the lanthanum-promoted zeolite beta.

Turning now to FIG. 1, there is illustrated a schematic block diagram of an alkylation/transalkylation process in which the regeneration procedure of the present invention can be employed. As shown in FIG. 1, a feed stream comprising a mixture of ethylene and benzene in a mole ratio of benzene to ethylene of about 1 to 15 is supplied via line 1 through a heat exchanger 2 to an alkylation reaction zone. Alkylation zone 4 preferably comprises one or more multi-stage reactors having a plurality of series-connected catalyst beds containing a zeolite beta alkylation catalyst, specifically a cerium promoted zeolite beta alkylation catalyst as described herein. The alkylation zone 4 is operated at temperature and, pressure conditions to maintain the alkylation reaction in the supercritical phase, i.e. the benzene is in the supercritical state, and at a feed rate to provide a space velocity enhancing diethylbenzene production while retarding by-products production. Preferably, the space velocity of the benzene feed stream will be within the range of 10–150 hrs.$^{-1}$ LHSV per bed.

The output from the alkylation reactor 4 is supplied via line 5 to an intermediate benzene separation zone 6 that may take the form of one or more distillation columns. Benzene is recovered through line 8 and recycled through line 1 to the alkylation reactor. The bottoms fraction from the benzene separation zone 6, which includes ethylbenzene and polyalkylated benzenes including polyethylbenzene, is supplied via line 9 to an ethylbenzene separation zone 10. The ethylbenzene separation zone may likewise comprise one or more sequentially connected distillation columns. The ethylbenzene is recovered through line 12 and applied for any suitable purpose, such as in the production of vinyl benzene. The bottoms fraction from the ethylbenzene separation zone 10, which comprises polyethylbenzene, principally diethylbenzene, is supplied via line 14 to a transalkylation reactor 16. Benzene is supplied to the transalkylation reaction zone through, line 18. The transalkylation reactor, which preferably is operated under liquid phase conditions, contains a molecular sieve catalyst, preferably zeolite-Y, which has a somewhat larger pore size than the cerium-modified zeolite beta used in the reaction alkylation zone. The output from the transalkylation reaction zone is recycled via line 20 to the benzene separation zone 6.

Figure 2:
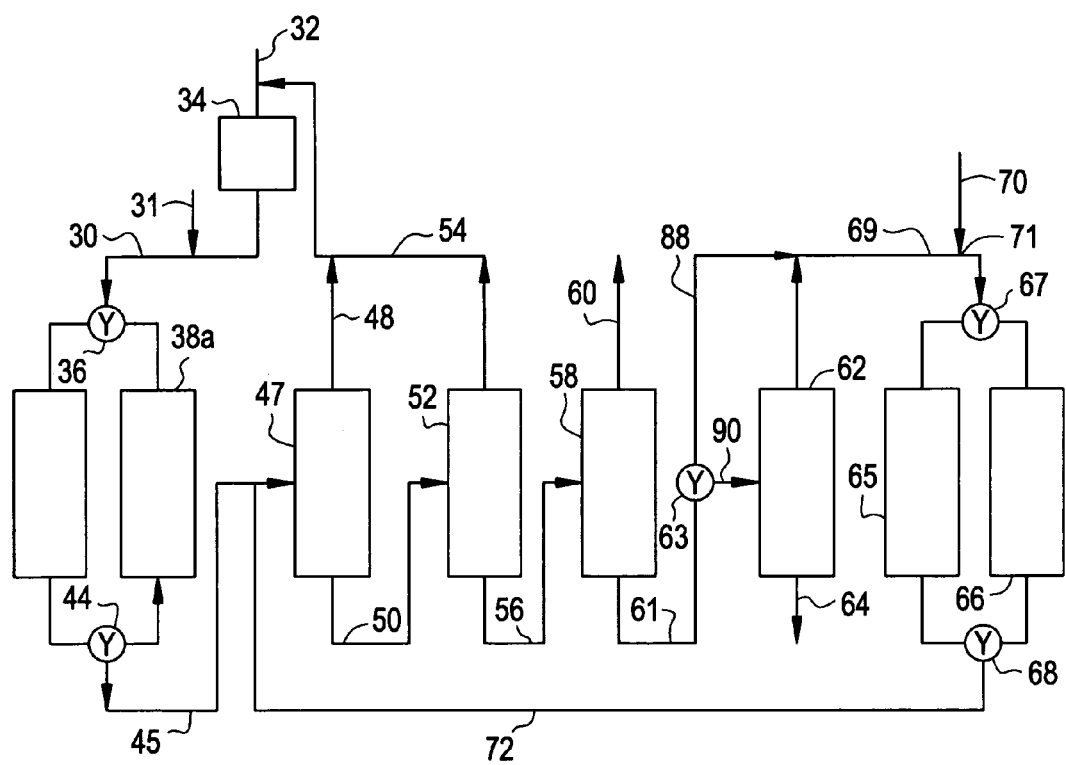
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the critical phase alkylation and transalkylation process. As shown in FIG. 2, an input feed stream is supplied with fresh ethylene through line 31 and fresh benzene through line 32. As noted previously, the fresh benzene stream supplied via line 32 preferably is of high purity containing at least 98 wt. %, preferably about 99 wt. %, benzene with no more than 1 wt. % other components. Typically, the fresh benzene stream will contain about 99.5 wt. % benzene, less than 0.5% ethylbenzene, with only trace amounts of non-aromatics and toluene. Line 32 is provided with a preheater 34 to heat the benzene stream consisting of fresh and recycled benzene to the desired temperature for the supercritical alkylation reaction. The feed stream is supplied through a two-way, three-position valve 36 and inlet line 30 to the top of one or both parallel critical phase alkylation reactor 38 and 38a comprising a plurality of series connected catalyst beds each of which contains the desired molecular sieve alkylation catalyst. The reactors are operated at an average temperature, preferably within the range of 250–350° C. inlet temperature and at pressure conditions of about 550 to 800 psia, to maintain the benzene in the critical phase. As mentioned previously, because of the high temperature structural integrity of cerium-promoted zeolite beta, the alkylation reaction zone can be operated at temperatures of up to about 500° C. and even beyond that to temperatures of about 540° C.

In normal operation of the system depicted in FIG. 2, both reaction zones 38 and 38a may, during most of a cycle of operation, be operated in a parallel mode of operation in which they are both in service at the same time. In this case, valve 36 is configured so that the input stream in line 30 is roughly split in two to provide flow to both reactors in approximately equal amounts. Periodically, one reactor is taken off-stream for regeneration of the catalyst in accordance with the present invention. Valve 36 is then configured so that all of the feed stream from line 30 can be supplied to reactor 38 while the catalyst beds in reactor 38a are regenerated and visa versa. The regeneration procedure normally takes place over a relatively short period of time relative to the operation of the reactor in the parallel alkylation mode. The regeneration procedure preferably is carried out at temperatures substantially in excess of those normally employed in the regeneration of zeolite beta-type catalysts. When regeneration of the catalyst beds in reactor 38a is completed, this catalyst can then be returned on-stream, and at an appropriate point, the reactor 38 can be taken off-stream for regeneration. This mode of operation involves operation of the individual reactors at relatively lower space velocities for prolonged periods of time with periodic relatively short periods of operation at enhanced, relatively higher space velocities when one reactor is taken off-stream. By way of example, during normal operation of the system with both reactors 38 and 38a on-stream, the feed stream is supplied to each reactor to provide a space velocity of about 25–45 hr.$^{-1}$ LHSV. When reactor 38a is taken off-stream and the feed rate continues unabated, the space velocity for reactor 38 will approximately double to 50–90 hr.$^{-1}$ LHSV. When the regeneration of reactor 38a is completed, it is placed back on-stream, and again the feed stream rate space velocity for each reactor will decrease to 25–45 hr.$^{-1}$ until such point as reactor 38 is taken off-stream, in which case the flow rate to reactor 38a will, of course, increase, resulting again in a transient space velocity in reactor 38 of about 50–90 hr.$^{-1}$ LHSV.

Figure 3:
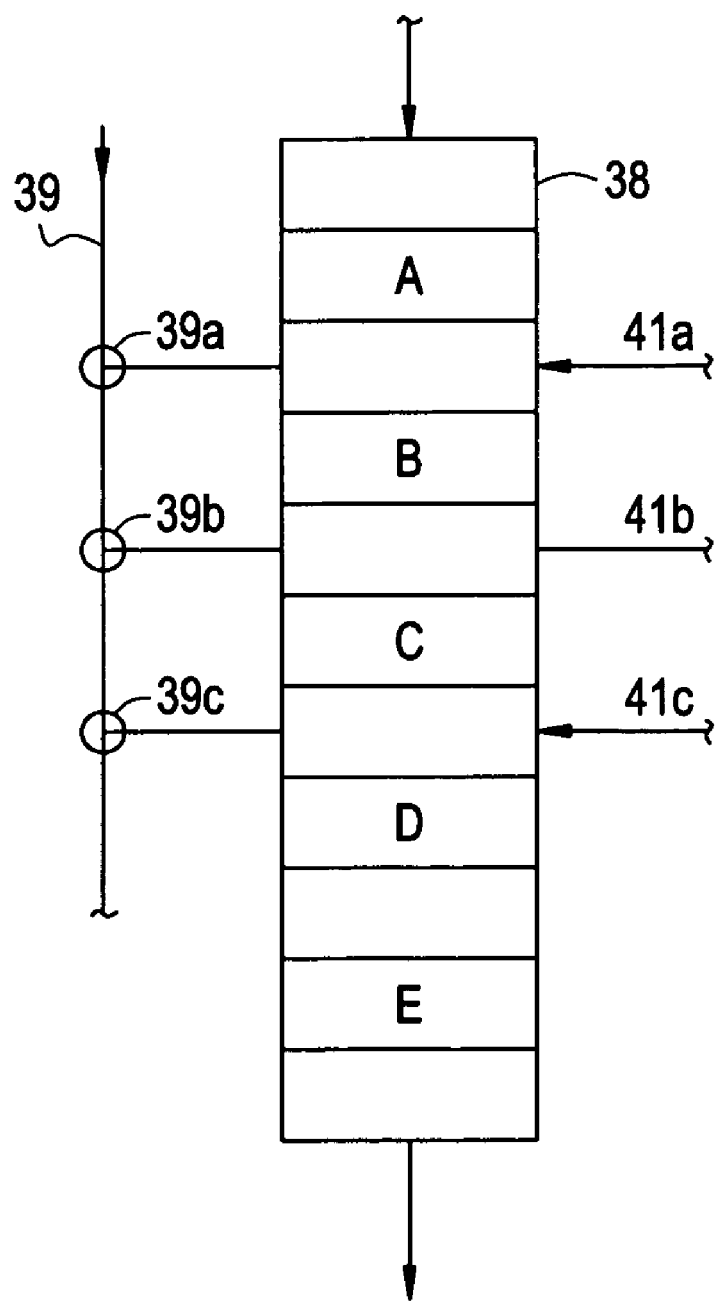
FIG. 3 is a schematic illustration of an alkylation reactor comprising a plurality of series connected catalyst beds with the interstage injection of feed components.

A preferred reactor configuration is shown in detail in FIG. 3. As illustrated there, the reactor 38 comprises five series connected catalyst beds designated as beds A, B, C, D, and E. A benzene-ethylene feed stream is supplied to the top of the reactor and into Bed A. Initially, however, it will be preferred to start the process with the injection of benzene without the presence of ethylene. Ethylene injection is initiated once a benzene environment has been established within the reaction zone. This presence of the substantial benzene atmosphere in the reaction zone, provides a site for the reaction of ethylene when it is added, thus minimizing reactions involving the dimerizition or trimerizition which could promote excess coking of the catalyst. An ethylene feed stream is supplied via line 39 and proportionating valves 39a, 39b and 39c to provide for the appropriate interstage injection of ethylene. The interstage injection of ethylene can be carried out in conjunction with the use of interstage heat exchangers to cool the effluent from the catalyst bed of one reaction stage as it is withdrawn from the reaction stage and introduced into the catalyst bed of the next succeeding reaction stage. The ethylene may be supplied to the effluent from one reaction stage prior to passage to the interstage heat exchanger as described in U.S. Pat. No. 5,073,653. For a further description of a suitable procedure for the interstage injection of ethylene in conjunction with cooling of the effluent from one stage to the next, reference is made to the aforementioned U.S. Pat. No. 5,073,653, the entire disclosure of which is incorporated herein by reference. Benzene can also be introduced between the catalyst stages by means of secondary benzene supply lines 41a, 41b and 41c, respectively. As will be recognized, the parallel reactor 38a will be configured with similar manifolding as shown in FIG. 3 with respect to reactor 38.

The rare earth promoted zeolite beta employed in the present invention is highly stable and retains it activity for prolonged periods of time. This is particularly true in the case of cerium promoted zeolite beta employed in the supercritical phase alkylation of benzene. Typical operation of the reactor in the alkylation mode will be for periods of time roughly 5–15 times the period of time in which regeneration is carried out. Because of the length of the alkylation run between regenerations, the coke initially laid down in the catalyst beds tends to age with hydrogen evolution as the reaction front moves through the catalyst bed. The result is a layer of relatively nonporous refractory coke deposited on the cerium promoted beta catalyst. As additional coke is laid down, it becomes progressively more porous with the coke deposited on the catalyst bed in the latter stages of the alkylation run being most porous. The regeneration procedure employed in the present invention is designed to provide a progressive procedure in which the more porous coke is burned off during an initial stage of the regeneration procedure followed by progressively burning off the more refractory coke in the later stages of the regeneration procedure. This may be accomplished in a step-wise mode involving the intermediate introduction of an inert gas such as nitrogen or in a continuum procedure in which a nitrogen and air stream is injected with the air content progressively increased. In either case, the result is to initially burn off the more porous coke in the initial portion of the regeneration procedure and to burn off the more refractory coke later in the procedure after the porous coke has been eliminated. This enables the regeneration procedure to be carried out while avoiding an initial intense high temperature exotherm in the catalyst bed, which would result from starting out to burn off the coke at a high temperature to eliminate all of the coke at once rather than continuously.

In one embodiment of the invention an incremental step-wise procedure is employed during which nitrogen and nitrogen-air mixtures are introduced sequentially with a nitrogen atmosphere produced between stages of air and nitrogen injection at progressively elevated temperatures. In carrying out this embodiment of the invention, prior to initiating the regeneration procedure, the ethylene injection into the reactor is terminated and a benzene injection is continued to provide a benzene effluent from the reactor, that is, to produce a relatively pure benzene atmosphere within the reactor. At this stage, the reactor outlet temperature of the catalyst bed in the reactor may be about 350° C. when ethylene injection is halted and will fall off to perhaps 310 to 320° C. Benzene injection is halted and nitrogen injection is then initiated with the nitrogen at an initial relatively low temperature, e.g., about 350° C. After nitrogen has continued to dry out the catalyst, air injection is started and ramped up to achieve an air-nitrogen mixture of about 50-volume percent air and 50-volume percent nitrogen. When the air-nitrogen mixture is injected into the reactor, the temperature is increased by perhaps 10 to 20° C. as a result of coke burned off the catalyst at the initial temperature of 350° C. This normally will be indicated by a slight rise in temperature at the outlet of the reactor with the temperature then returning to the temperature of the initial nitrogen injection temperature—that is about 350° C. Thereafter, air injection is terminated and nitrogen is injected at an elevated temperature, preferably one which is greater incrementally than the initial nitrogen temperature by about 75 to 150° C. Specifically, in the example given here, the nitrogen temperature is increased from 350° C. to about 475° C.

The air content is then increased progressively to produce a 50–50 mixture of air and nitrogen with the attendant production of an exotherm of about 10–20° C. above the injection temperature of 475° C. After the exotherm moves through the catalyst bed at this temperature, air injection is terminated and the temperature of the injected nitrogen is again increased. Preferably, this increase is by an amount which is incrementally less than the temperature of the previous increase. Thus, in the example given where the nitrogen temperature was increased from 350° C. to 475° C., the incremental increase in temperature at this stage would be about 50° C. to inject the pure nitrogen at a temperature of 525° C. Air is then added to provide a 50–50 mixture of air and nitrogen with an exotherm again produced by an incremental amount of about 10–20° C. above the 525° C. set point. Air and nitrogen injection is continued until this exotherm moves through the catalyst bed, at which stage air injection is terminated and the nitrogen temperature is again increased, preferably by an amount which is less than the incremental amount of the previous increase. Thus, the nitrogen temperature may be increased from 525° C. to about 550–560° C. The air content is then increased to arrive at a 50–50 mixture of air and nitrogen and this mixture is continued until the exotherm of about 10–20° C. moves through the catalyst bed. Thereafter, air injection is terminated and the temperature of the injected nitrogen is decreased usually to ambient temperature conditions. Nitrogen injection is then terminated and the catalyst bed is ready for another alkylation run.

In another embodiment of the present invention, after stopping ethylene and then benzene injection, nitrogen injection is initiated at the start of the regeneration procedure at a high temperature which can remain constant throughout the regeneration procedure or which can be increased although by smaller incremental increases than in the case of the former embodiment in which pure nitrogen is injected between stages of air and nitrogen mixtures. In this embodiment of the invention, the nitrogen temperature is started out at a high temperature and then maintained at this temperature with the air added to the nitrogen to progressively increase the air content in very small increments. By way of example, nitrogen injection is carried out at an initial temperature of at least 500° C., preferably about 550–575° C., and continued for a time to bring all or a part of the catalyst bed up to this temperature at which time a very small amount of air is added to the nitrogen stream. Thus, air may be added to provide a mixture of 1 volume percent air and 99 volume percent nitrogen with the air content increased in a continuum or in a series of small steps until a final set point of 40%–60% air, specifically 50% air and 50% nitrogen, is reached. By way of example, the air content may be increased in ten to fifteen steps at increments of about 3–5 volume percent. By following this regimen, the more combustible high porosity coke is initially burned off of the catalyst bed in the environment of low air content with the less porous more refractory coke becoming progressively burned off of the catalyst bed as the air content is increased. At the conclusion of the regeneration procedure, when the exotherm is moved completely through the catalyst bed, the air injection is terminated and nitrogen injection is continued at reduced temperatures similarly as described above with respect to the first embodiment of the invention. Typically, the nitrogen or mixture of nitrogen and air is passed through the catalyst bed at a gas hourly space velocity (GHSV) within the range of 1,500–5,000 hrs.$^{-1}$ Returning to FIG. 2, the effluent stream from one or both of the alkylation reactors 38 and 38a is supplied through a two-way, three-position outlet valve 44 and outlet line 45 to a two-stage benzene recovery zone which comprises as the first stage a prefractionation column 47. Column 47 is operated to provide a light overhead fraction including benzene which is supplied via line 48 to the input side of heater 34 where it is mixed with benzene in line 32 and then to the alkylation reactor input line 30. A heavier liquid fraction containing benzene, ethylbenzene and polyethylbenzene is supplied via line 50 to the second stage 52 of the benzene separation zone. Stages 47 and 52 may take the form of distillation columns of any suitable type, typically, columns having from about 20–60 trays. The overhead fraction from column 52 contains the remaining benzene, which is recycled via line 54 to the alkylation reactor input. Thus, lines 48 and 54 correspond to the output line 8 of FIG. 1. The heavier bottoms fraction from column 52 is supplied via line 56 to a secondary separation zone 58 for the recovery of ethylbenzene. The overhead fraction from column 58 comprises relatively pure ethylbenzene, which is supplied to storage or to any suitable product destination by way of line 60. By way of example, the ethylbenzene may be used as a feed stream to a styrene plant in which styrene is produced by the dehydrogenation of ethylbenzene. The bottoms fraction containing polyethylbenzenes, heavier aromatics such as cumene and butyl benzene, and normally only a small amount of ethylbenzene is supplied through line 61 to a tertiary polyethylbenzene separation zone 62. As described below, line 61 is provided with a proportioning valve 63 which can be used to divert a portion of the bottoms fraction directly to the transalkylation reactor. The bottoms fraction of column 62 comprises a residue, which can be withdrawn from the process via line 64 for further use in any suitable manner. The overhead fraction from column 62 comprises a polyalkylated aromatic component containing diethylbenzene and a smaller amount of triethylbenzene and a minor amount of ethylbenzene is supplied to an on stream transalkylation reaction zone. Similarly as described above with respect to the alkylation reactors, parallel transalkylation reactors 65 and 66 are provided through inlet and outlet manifolding involving valves 67 and 68. Both of reactors 65 and 66 can be placed on stream at the same time so that both are in service in a parallel mode of operation. Alternatively, only one transalkylation reactor can be on-stream with the other undergoing regeneration operation in order to burn coke off the catalyst beds. By minimizing the amount of ethylbenzene recovered from the bottom of column 58, the ethylbenzene content of the transalkylation feed stream can be kept small in order to drive the transalkylation reaction in the direction of ethylbenzene production. The polyethylbenzene fraction withdrawn overhead from column 62 is supplied through line 69 and mixed with benzene supplied via line 70. This mixture is then supplied to the on-line transalkylation reactor 65 via line 71. Preferably, the benzene feed supplied via line 70 is of relatively low water content, about 0.05 wt. % or less. Preferably, the water content is reduced to a level of about 0.02 wt. % or less and more preferably to less than 0.01 wt. %, down to 0.002 wt. % or less. The transalkylation reactor is operated as described before in order to maintain the benzene and alkylated benzenes within the transalkylation reactor in the liquid phase. Typically, the transalkylation reactor may be operated to provide an average temperature within the transalkylation reactor of about 65°–290° C. and an average pressure of about 600 psi. The preferred catalyst employed in the transalkylation reactor is zeolite Y. The weight ratio of benzene to polyethylbenzene should be at least 1:1 and preferably is within the range of 1:1 to 4:1.

The output from the transalkylation reactor or reactors containing benzene, ethylbenzene, and diminished amounts of polyethylbenzene is recovered through line 72. Typically, line 72 will be connected to the inlet lines 47a for recycle to the prefractionation column 47 as shown. However, the effluent from the liquid-phase transalkylation reactor may be supplied to either or both of distillation columns 47 and 52.

Returning to the operation of the separation system, in one mode of operation the entire bottoms fraction from the ethylbenzene separation column 58 is applied to the tertiary separation column 62 with overhead fractions from this zone then applied to the transalkylation reactor. This mode of operation offers the advantage of relatively long cycle lengths of the catalyst in the transalkylation reactor between regeneration of the catalyst to increase the catalyst activity. Another mode of operation achieves this advantage by supplying a portion of the output from the ethylbenzene separation column 58 through valve 63 directly to the transalkylation reactor.

As shown in FIG. 2, a portion of the bottoms fraction from the secondary separation zone 58 bypasses column 62 and is supplied directly to the transalkylation reactor 65 via valve 63 and line 88. A second portion of the bottoms fraction from the ethylbenzene column is applied to the tertiary separation column 62 through valve 63 and line 90. The overhead fraction from column 62 is commingled with the bypass effluent in line 88 and the resulting mixture is fed to the transalkylation reactor via line 67. In this mode of operation a substantial amount of the bottoms product from column 58 can be sent directly to the transalkylation reactor, bypassing the polyethylbenzene column 62. Normally, the weight ratio of the first portion supplied via line 88 directly to the transalkylation reactor to the second portion supplied initially via line 90 to the polyethylbenzene column would be within the range of about 1:2 to about 2:1. However, the relative amounts may vary more widely to be within the range of a weight ratio of the first portion to the second portion in a ratio of about 1:3 to 3:1.

The molecular sieve catalyst employed in the critical phase alkylation reactor is a zeolite beta catalyst that can be a conventional zeolite beta but preferably is a rare earth promoted beta, more preferably a zeolite beta modified by the inclusion of cerium as described below. The cerium-promoted zeolite beta catalyst will normally be formulated in extrudate pellets of a size of about ⅛-inch or less, employing a binder such as silica or alumina. A preferred form of binder is silica, which results in catalysts having somewhat enhanced deactivation and regeneration characteristics when compared with zeolite beta formulated with a conventional alumina binder. Typical catalyst formulations may include about 20 wt. % binder and about 80 wt. % molecular sieve. The catalyst employed in the transalkylation reactor normally will take the form of a zeolite Y catalyst, such as zeolite Y or ultra-stable zeolite Y. Various zeolites of the Y and beta types are in themselves well known in the art. For example, zeolite Y is disclosed in U.S. Pat. No. 4,185,040 to Ward, and zeolite beta is disclosed in U.S. Pat. No. 3,308,069 to Wadlinger and U.S. Pat. No. 4,642,226 to Calvert et al.

Cerium-promoted zeolite beta employed in the critical phase alkylation reactor can be a zeolite beta of the type described in Wadlinger or Calvert, which has been modified by the inclusion of cerium in the crystalline framework. The cerium-promoted zeolite beta can be based on a high silica/alumina ratio zeolite beta or a ZSM-12 modified zeolite beta as described in detail below.

Basic procedures for the preparation of zeolite beta are well known to those skilled in the art. Such procedures are disclosed in the aforementioned U.S. Pat. No. 3,308,069 to Wadlinger et al and U.S. Pat. No. 4,642,226 to Calvert et al and European Patent Publication No. 159,846 to Reuben, the disclosures of which are incorporated herein by reference. The zeolite beta can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al, zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. Unless steps are taken to minimize the alumina content, the resulting zeolite beta is normally characterized by a silica to alumina molar ratio (expressed as $SiO_2/Al_2O_3$) of between about 20 and 50.

The zeolite beta is then subjected to ion exchange with ammonium ions at uncontrolled pH. It is preferred that an aqueous solution of an inorganic ammonium salt, e.g., ammonium nitrate, be employed as the ion-exchange medium. Following the ammonium ion-exchange treatment, the zeolite beta is filtered, washed and dried, and then calcined at a temperature between about 530° C. and 580° C. for a period of two or more hours.

Zeolite beta can be characterized by its crystal structure symmetry and by its x-ray diffraction patterns. Zeolite beta is a molecular sieve of medium pore size, about 5–6 angstroms, and contains 12-ring channel systems. Zeolite beta is of tetragonal symmetry $P4_122$, a=12.7, c=26.4 Å (W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The framework topology of zeolite beta," *Zeolites*, 1988, Vol. 8, November, pp. 446–452, the entire disclosure of which is incorporated herein by reference.

The cerium-promoted zeolite beta employed in carrying out the present invention may be based upon conventional zeolite beta, such as disclosed in the aforementioned patent to Calvert et al. For a further description of procedures for producing zeolite beta useful in accordance with the present invention, reference is made to the aforementioned U.S. Pat. No. 3,308,069 to Wadlinger, U.S. Pat. No. 4,642,226 to Calvert, and U.S. Pat. No. 5,907,073 to Ghosh and EPA Publication No. 507,761 to Shamshoum, the entire disclosures of which are incorporated herein by reference.

The invention can also be carried out with a zeolite beta having a higher silica/alumina ratio than that normally encountered. For example, as disclosed in EPA Publication No. 186,447 to Kennedy, a calcined zeolite beta can be dealuminated by a steaming procedure in order to enhance the silica/alumina ratio of the zeolite. Thus, as disclosed in Kennedy, a calcined zeolite beta having a silica/alumina ratio of 30:1 was subjected to steam treatment at 650° C. and 100% steam for 24 hours at atmospheric pressure. The result was a catalyst having a silica/alumina ratio of about 228:1, which was then subjected to an acid washing process to produce a zeolite beta of 250:1. Various zeolite betas, such as described above, can be subject to extraction procedures in order to extract aluminum from the zeolite beta framework by extraction with nitric acid. Acid washing of the zeolite beta is carried out initially to arrive at a high silica/alumina ratio zeolite beta. This is followed by ion-exchanging cerium into the zeolite framework. There should be no subsequent acid washing in order to avoid removing cerium from the zeolite.

The procedure disclosed in EP 507,761 to Shamshoum, et al for incorporation of lanthanum into zeolite beta can be employed to produce cerium promoted zeolite beta. Thus, cerium nitrate may be dissolved in deionized water and then added to a suspension of zeolite beta in deionized water following the protocol disclosed in EP 507,761 for the incorporation of lanthanum into zeolite beta by ion exchange. Following the ion exchange procedure, the cerium exchanged zeolite beta can then be filtered from solution washed with deionized water and then dried at a temperature of 110° C. The powdered cerium exchanged zeolite beta can then be molded with an aluminum or silicon binding agent followed by extrusion into pellet form.

In experimental work carried out respecting the present invention alkylation reactor runs were carried out employing a single stage alkylation reactor. The reactor operated as a laboratory simulation of the single stage of a multiple stage reactor of the type illustrated in FIG. 3. In carrying out the experimental work a cerium promoted zeolite beta having a silica alumina ratio of 150 and a cerium/aluminum atomic ratio of 0.75 was employed. This catalyst was formed employing a silica binder. Additional experimental work was carried out employing a lanthanum promoted zeolite beta catalyst, also having a silica alumina ratio of 150 and having a lanthanum/aluminum atomic ratio of 1.0 formulated with a silica binder.

The cerium promoted zeolite beta was used in the alkylation reactor through seven regenerations for a total cumulative time of in excess of 250 days. Throughout the successive runs the inlet temperature of the reactor was about 305° C.±5° C. and the temperature at the outlet, of the reactor was about 340° C.±10° C. resulting in an incremental temperature increase across the reactor of about 30° C.–40° C. The reactor was operated at an inlet pressure of about 595–600 PSIG with a pressure gradient across the reactor of only a few pounds per square inch.

The lanthanum promoted zeolite beta was employed in a test run spanning about 85 days on line with regeneration of the catalyst at the conclusion of 20 and 60 days. The lanthanum promoted zeolite beta had a silica alumina ratio of 150 and a lanthanum/aluminum atomic ratio of 1.0.

Figure 4:
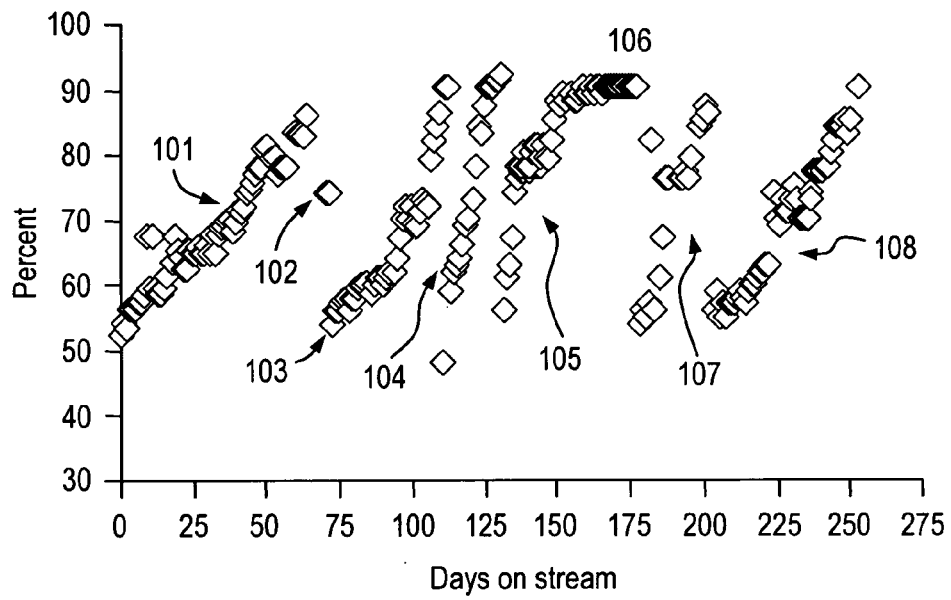
FIG. 4 is a graph illustrating the percent of bed used versus days on stream for an alkylation reaction carried out with a cerium modified zeolite beta.

The results of the experimental work carried out with the cerium beta catalyst and the lanthanum beta catalyst are illustrated in FIGS. 4–11. In some cases, comparative data is presented for gas phase alkylation carried out employing a silicalite catalyst having a silica/alumina ratio of about 125. The silicalite catalyst was employed under temperature and pressure conditions of about 450° C. and 300 psig. Turning initially to FIG. 4 the percent of the bed used in the catalytic reaction is plotted on the ordinate versus the total cumulative days on stream on the abscissa. The percent of the catalyst bed was calculated based upon the maximum temperature sensed across the bed employing 6 temperature sensors spaced from the inlet to the outlet of the reactor. The percent of the bed used was calculated based upon the maximum temperature sensed at the temperature sensors across the bed. In FIG. 4 Curve 101 indicates the percent of bed used during the use of the fresh catalyst for an initial period of about 64 days. Curves 102, 103, 104, 105, 106, 107 and 108 show the results obtained after successive regeneration of the catalysts. Curve 106 indicates the results obtained for the catalyst after being regenerated by a high temperature regeneration procedure as described below in more detail with respect to FIG. 6.

Figure 5:
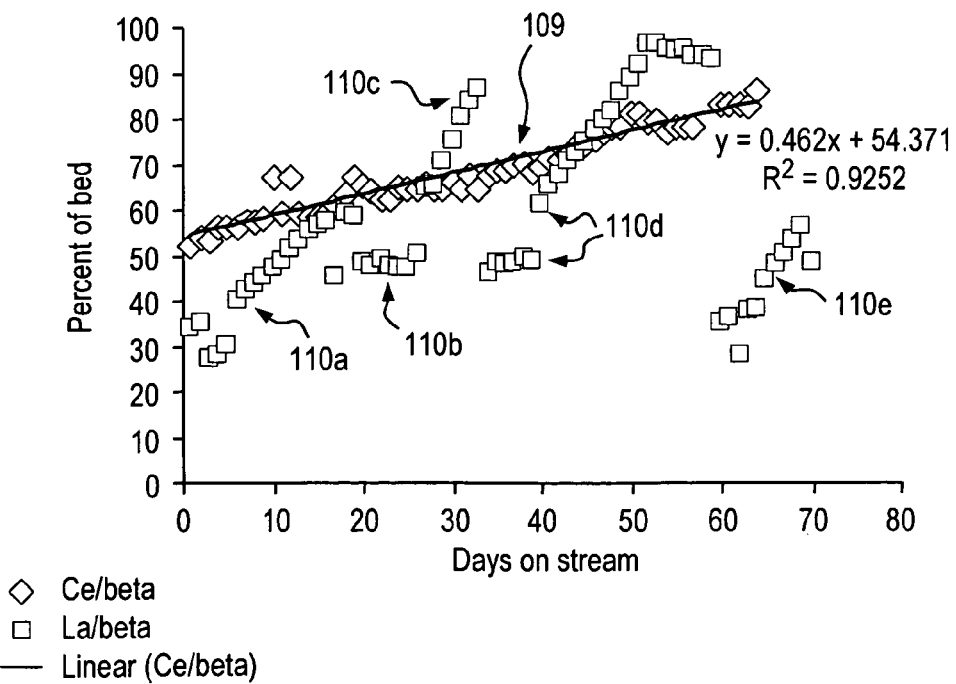
FIG. 5 is a graph showing the percent of bed used for both a cerium modified zeolite beta and a lanthanum modified zeolite beta.

FIG. 5 shows the catalyst bed used in the catalytic reaction as a function of days on stream for the fresh cerium beta catalyst indicated by Curve 109 corresponding to Curve 101 in FIG. 4, versus results obtained for lanthanum beta indicated by Curve 110. Curve 110 shows the results for fresh catalyst (110a), and successively regenerated lanthanum promoted beta catalyst indicated by Curves 110b, 110c, 110c, 110d and 110e. As can be seen from a comparison of Curves 109 and 110 the cerium promoted zeolite beta had a much higher stability over a prolonged period of time than exhibited by lanthanum beta over a series of successive regenerations.

Figure 6:
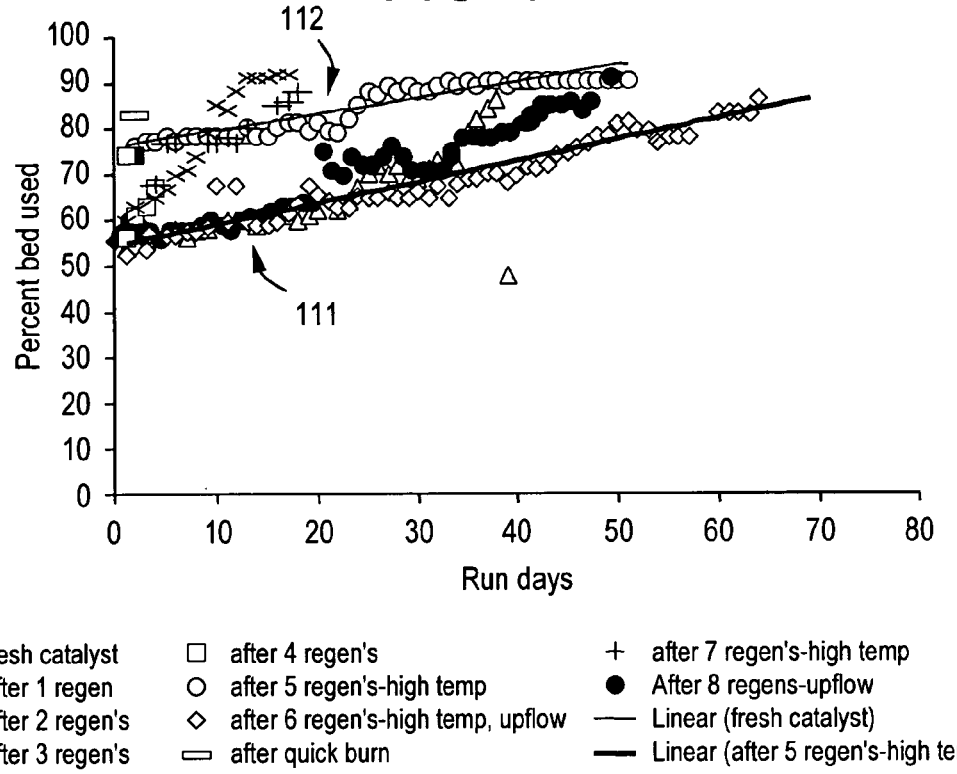
FIG. 6 is a graph showing the percent of bed used for cerium modified zeolite beta employed as a fresh catalyst and as a regenerated catalyst.

FIG. 6 shows the percent of bed used plotted on the ordinate versus run time in days plotted on the abscissa for the fresh cerium promoted zeolite beta and for the catalyst after each regeneration. In each case, the days elapsed after initiation with a fresh catalyst, and after initiation after each regeneration are shown. In FIG. 6 Curves 111 and 112 are linear plots for the fresh catalyst (Curve 111) and for the catalyst after five (5) regenerations with the last regeneration being carried out under high temperature conditions (Curve 112). As can be seen from an examination of the data shown in FIG. 6, after regeneration under normal temperature conditions at maximum temperature of about 475° C., the cerium promoted zeolite beta deactivated very rapidly. However, for the catalyst regenerated under the high temperature conditions in accordance with the present invention at a maximum temperature about 530° C., the catalyst deactivation rate corresponded generally to the catalyst deactivation observed for the fresh catalyst.

Figure 7:
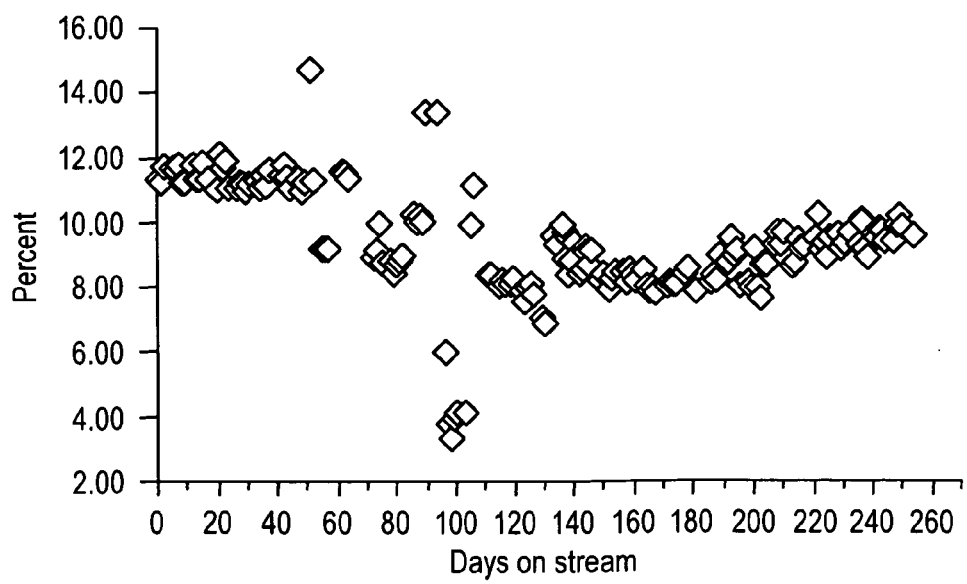
FIG. 7 is a graph showing an ethyl benzene yield versus days on stream for a cerium modified zeolite beta.

FIG. 7 shows the ethyl benzene yield, EB, in terms of percent conversion plotted on the ordinate versus the total cumulative days on stream for the cerium promoted zeolite beta indicated by data points ♦. It will be recognized that the days on stream can be correlated with the regeneration data shown in FIG. 4. Thus, the fresh catalyst showed essentially a constant ethyl benzene conversion over the 64 day run carried out with the fresh catalyst. The anomalous results showing an ethyl benzene conversion at about 9% for days 55, 56 and 57 correlated with an inadvertent shutdown of the reactor. Subsequent regenerations resulted in good stability after each regeneration.

Figure 8:
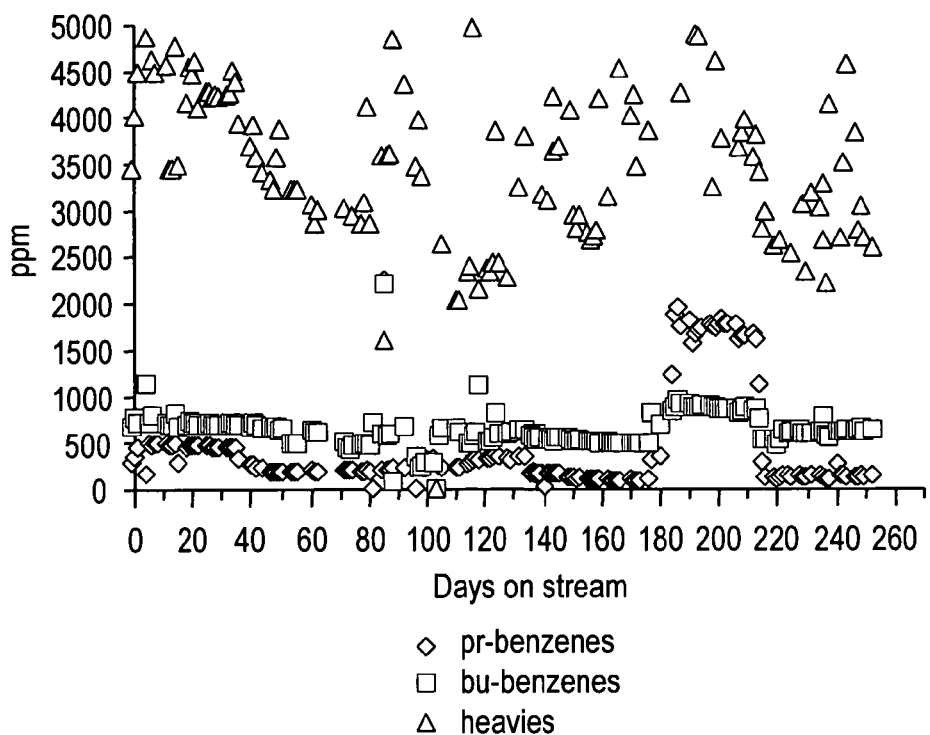
FIG. 8 is a graph illustrating by-product yield versus days on stream for a cerium modified zeolite beta.

FIG. 8 shows for the cerium promoted zeolite beta the by-product yield, BP, relative to ethyl benzene plotted in parts per million plotted on the ordinate versus days on stream for propyl benzene, ♦, butyl benzene, ■, and heavy components, ▲, for the 250 day run. As can be seen, the butyl benzene yield was, generally less than 1000 ppm and the propyl benzene yield less than 500 ppm over the run time of 250+ days. The heavies yield varied from about 5000 ppm to about 2000 ppm or slightly less. As discussed below these values are substantially better than the corresponding values observed for the lanthanum promoted zeolite beta.

Figure 9:
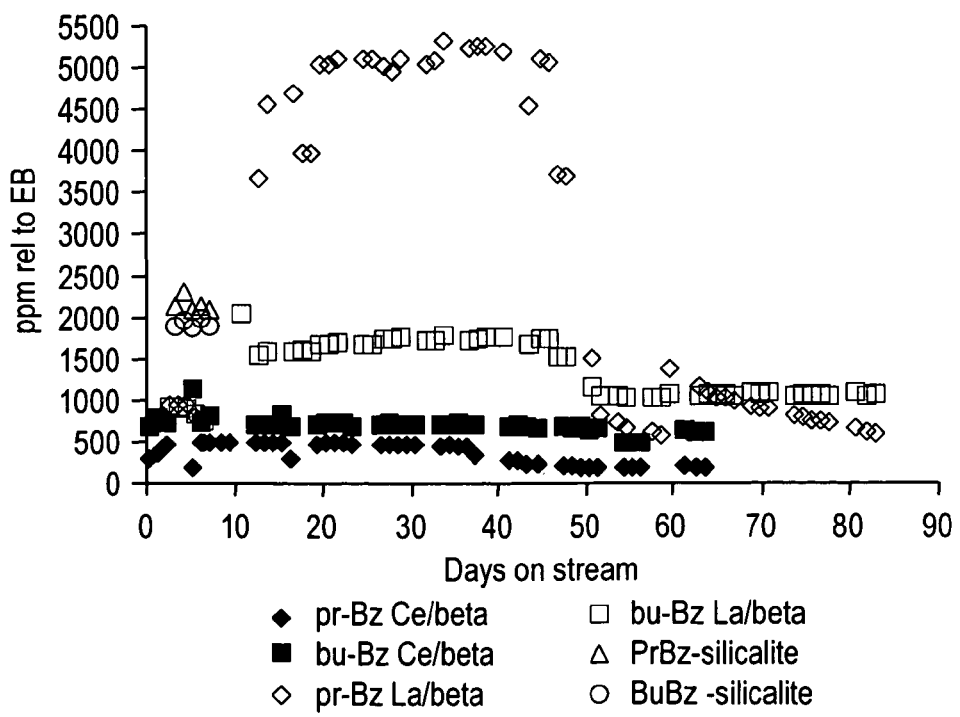
FIG. 9 is a graph showing comparative by-product yields versus days on stream for cerium modified zeolite beta, lanthanum modified zeolite beta, and a silicalite catalyst.
Figure 10:
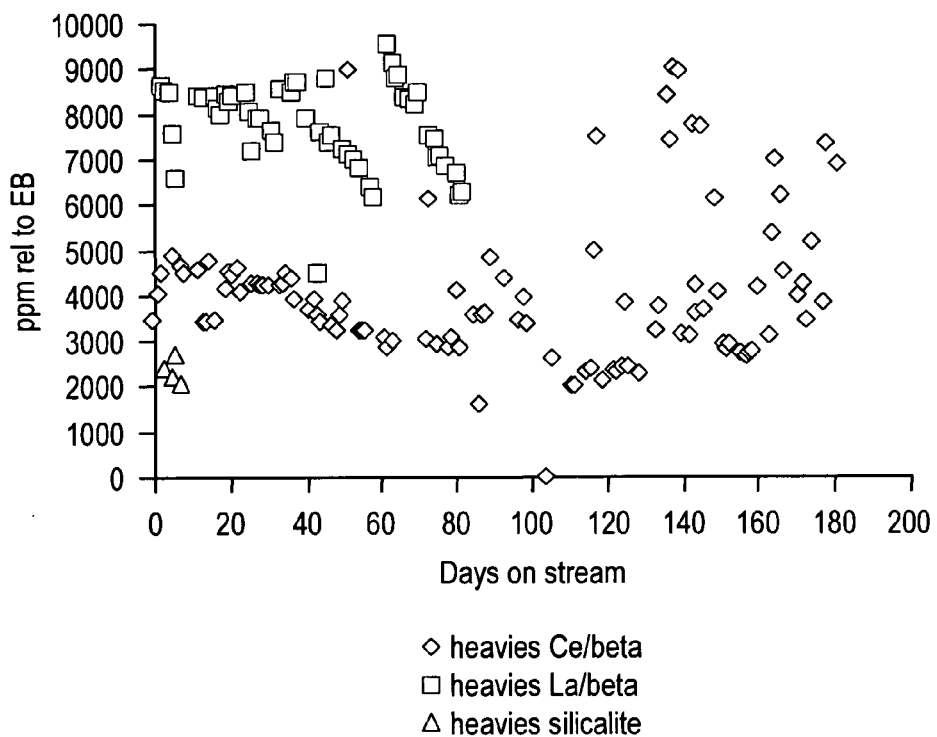
FIG. 10 is a graph showing a heavy by-product yield for cerium modified zeolite beta, lanthanum modified zeolite beta, and a silicalite catalyst.

The results for the propyl and butyl benzenes for the cerium promoted beta and the lanthanum promoted beta over 80+ days in comparison with the silicalite catalyst over a short time period (less than 10 days), are illustrated in FIG. 9. FIG. 9 is a plot of the designated by-products in ppm relative to ethyl benzene plotted on the ordinate versus the days on stream on the abscissa. FIG. 10 shows corresponding data for the heavies for the cerium beta and the lanthanum beta in comparison with the silicalite catalyst. As can be seen from examination of the data in FIGS. 9 and 10 the cerium beta alkylation catalyst showed substantially lower by-products yields in each of the three (3) categories as was the case for the lanthanum promoted beta. Specifically, the composite by-product yield of propylbenzene and butylbenzene produced during supercritical phase alkylation over the cerium-promoted zeolite beta was less than one-half of the corresponding by-product yield of propylbenzene and butylbenzene observed for the lanthanum-promoted zeolite beta.

Figure 11:
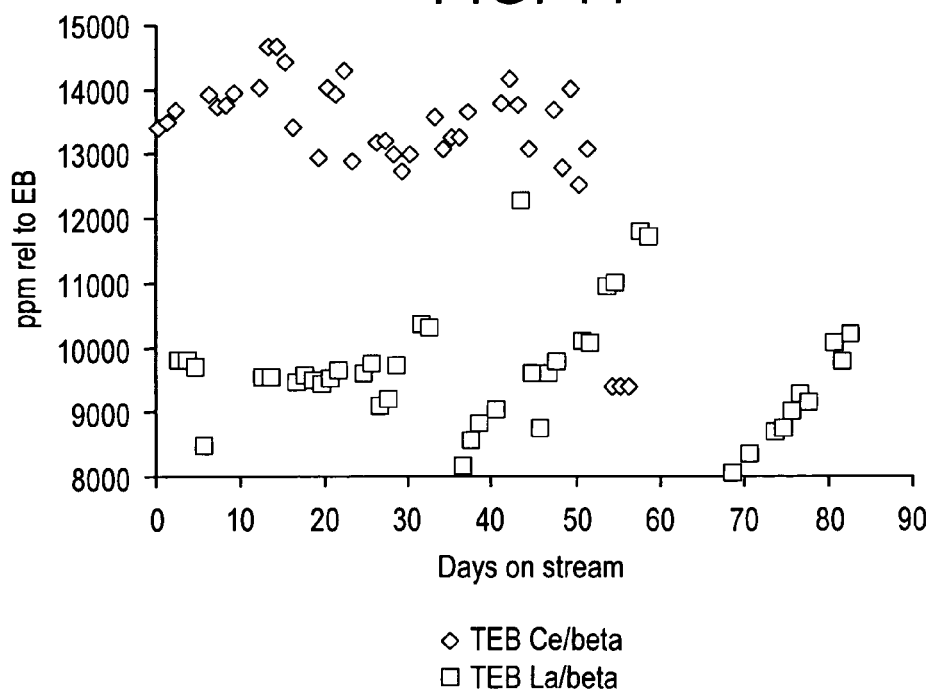
FIG. 11 is a graph illustrating the yield of triethyl benzene versus days on stream for cerium modified zeolite beta and lanthanum modified zeolite beta.

FIG. 11 illustrates the triethyl benzene yield (TEB) in parts per million relative to ethyl benzene plotted on the ordinate versus the time on stream in days plotted on the abscissa. The data for the cerium beta catalyst was plotted for the first 52 days of the run carried out with the fresh catalyst. The data for the lanthanum beta zeolite shows results for lanthanum beta over 83 days after a series of regenerations. As can be seen from an examination of FIGS. 9, 10 and 11 the substantially improved characteristics of the cerium promoted beta over the lanthanum promoted beta in terms of the heavy by-product yield comes at the expense of a moderately higher triethlybenzene production for the cerium beta.

Having described specific embodiments of the present invention, it will be understood that modifications thereof may be suggested to those skilled in the art, and it is intended to cover all such modifications as fall within the scope of the appended claims.

What is claimed is:

1. A process for the regeneration of a deactivated zeolite beta catalyst comprising:
   (a) providing a catalyst bed of a zeolite beta hydrocarbon conversion catalyst which has been deactivated in a hydrocarbon conversion reaction by the deposition of coke on the zeolite beta catalyst, said coke having a porosity characteristic ranging from a relatively porous coke constituent to a relatively less porous refractory coke constituent;
   (b) heating said zeolite beta to an elevated temperature in excess of 300° C. in an inert environment which is substantially free of oxygen;
   (c) thereafter supplying an oxidative regeneration gas comprising a mixture of an oxygen containing gas and an inert gas through said catalyst bed to oxidize at least a portion of the relatively porous coke component at a temperature greater than the temperature in subparagraph (b) and produce an exotherm which moves through said catalyst bed;
   (d) continuing the passage of said regeneration gas through said catalyst bed to result in decoking of said zeolite catalyst within said bed while progressively increasing at least one of the temperature and the oxygen content of said regeneration gas to oxidize a less porous component of said coke with the production of an exotherm which passes through said catalyst bed;
   (e) thereafter supplying a regeneration gas comprising a mixture of an oxygen containing gas and an inert gas having at least an increased oxygen content or an increased temperature greater than the temperature or oxygen content in subparagraph (d) to oxidize a less porous refractory component of said coke; and
   (f) thereafter further diminishing the oxygen content of said regeneration gas and passing an inert gas through said catalyst bed at a reduced temperature.

2. The method of claim 1 wherein the ratio of oxygen-containing gas to inert gas is progressively increasing in the course of the operation of subparagraph (d).

3. The method of claim 2 wherein the oxygen-containing gas is air and the inert gas is nitrogen.

4. The method of claim 3 wherein the air content of said regeneration gas is progressively increased until the air content is within the range of 40–60 vol. %.

5. The method of claim 4 wherein said regeneration gas is introduced into said catalyst bed at a temperature of at least 500° C. and has an initial air content of no more than 5 vol. %.

6. The method of claim 1 wherein said zeolite beta catalyst is a rare earth promoted zeolite beta.

7. The method of claim 6 wherein said zeolite beta catalyst is promoted with lanthanum or cerium.

8. The method of claim 7 wherein said zeolite beta catalyst is a cerium promoted zeolite beta.

9. The method of claim 8 wherein said cerium promoted zeolite beta catalyst has a silica/alumina mole ratio within the range of 50–200.

10. The process of claim 9 wherein said catalyst has a cerium/aluminum atomic ratio within the range of 0.5–1.5.

11. The method of claim 1 wherein said zeolite beta catalyst in the catalyst bed of subparagraph (a) has been deactivated by use of the catalyst in the reaction of a $C_2$–$C_4$ alkylating agent with an aromatic substrate.

12. The method of claim 11 wherein said alkylating agent is ethylene or propylene, and said aromatic substrate is benzene.

13. The method of claim 11 wherein said alkylating agent is ethylene and said aromatic substrate is benzene.

14. The process of claim 1 further comprising subsequent to subparagraph (d) and prior to subparagraph (e) introducing an inert gas into said reaction zone at a temperature greater than the temperature in subparagraph (b).

15. The process of claim 14 wherein said inert gas introduced into said reaction zone is at a temperature of at least 50° C. greater than the temperature in subparagraph (b) of claim 1.

* * * * *